(12) United States Patent
Engell

(10) Patent No.: US 8,536,375 B2
(45) Date of Patent: Sep. 17, 2013

(54) SYNTHESIS OF OBTAINING MODIFIED POLYETHYLENE GLYCOL INTERMEDIATES

(75) Inventor: Torgrim Engell, Oslo (NO)

(73) Assignee: GE Healthcare Limited, Amersham (GB)

( * ) Notice: Subject to any disclaimer, the term of this patent is extended or adjusted under 35 U.S.C. 154(b) by 252 days.

(21) Appl. No.: 13/141,337

(22) PCT Filed: Dec. 7, 2009

(86) PCT No.: PCT/US2009/066917
§ 371 (c)(1),
(2), (4) Date: Jun. 22, 2011

(87) PCT Pub. No.: WO2010/074935
PCT Pub. Date: Jul. 1, 2010

(65) Prior Publication Data
US 2012/0004423 A1     Jan. 5, 2012

Related U.S. Application Data

(60) Provisional application No. 61/139,689, filed on Dec. 22, 2008.

(51) Int. Cl.
*C07C 229/26* (2006.01)
*C07D 403/12* (2006.01)

(52) U.S. Cl.
USPC .......................................... 562/564; 548/462

(58) Field of Classification Search
USPC .......................................... 562/564; 548/462
See application file for complete search history.

(56) References Cited

U.S. PATENT DOCUMENTS

| | | |
|---|---|---|
| 6,858,409 B1 | 2/2005 | Thompson et al. |
| 8,415,510 B2 * | 4/2013 | Engell ........................ 568/852 |
| 2005/0175682 A1 | 8/2005 | Heyes et al. |

FOREIGN PATENT DOCUMENTS

| | | |
|---|---|---|
| WO | WO 92/16221 | 10/1992 |
| WO | WO 2009/108484 | 9/2009 |

OTHER PUBLICATIONS

Topchiyeva, I., Polymer Science USSR, (1990), 32(5):833-851.

* cited by examiner

*Primary Examiner* — Shailendra Kumar
(74) *Attorney, Agent, or Firm* — Yonggang Ji

(57) ABSTRACT

The present invention provides novel and more efficient synthesis's for obtaining an intermediate in the synthesis of obtaining a protecting group aminoxy PEG linker.

7 Claims, No Drawings

US 8,536,375 B2

SYNTHESIS OF OBTAINING MODIFIED POLYETHYLENE GLYCOL INTERMEDIATES

CROSS-REFERENCE TO RELATED APPLICATIONS

This application is a filing under 35 U.S.C. §371 and claims priority to international patent application number PCT/US2009/066917 filed Dec. 7, 2009, published on Jul. 1, 2010 as WO 2010/074935, which claims priority to U.S. provisional patent application number 61/139,689 filed Dec. 22, 2008.

FIELD OF THE INVENTION

The present invention provides a novel synthesis for obtaining intermediates for making an aminooxy PEGylated linker by synthesizing modified polyethylene glycols.

BACKGROUND OF THE INVENTION

The preparation of biomolecules, such as peptides or oligonucleotides, and other organic compounds on a solid matrix is better performed using bifunctional spacer molecules known as linkers. One of the two reactive functionalities of a linker is permanently attached to a suitably functionalized resin, most often through a stable amide bond, while the growing molecule is temporarily linked at the other reactive position of the linker.

Although the majority of linkers rely on acidolysis for the release of the final molecule from the support, the use of different mechanisms (e.g. photolysis, fluoridolysis, and base-catalyzed Beta-elimination) has been exploited for the final cleavage.

Additionally it is important to point out that biologically active molecules that selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumors, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (RGD). The RGD Sequence appears to act as a primary recognition site between the ligands presenting this sequence and receptors on the surface of cells. It is generally believed that secondary interactions between the ligand and receptor enhance the specificity or the interaction. These secondary interactions might take place between moieties of the ligand and receptor that are immediately adjacent to the RGD sequence or at sites that are distant from the RGD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO06/030291 relates to the use of peptide-based compounds as targeting vectors that bind to receptors associated with angiogenesis. Additionally, WO 2006/030291 describes peptide-based compounds having utility for diagnostic imaging which may be prepared rapidly. The present invention describes novel synthesis's of obtaining intermediates for obtaining a modified Boc-protected aminoxy, —COOCH(CH$_3$)$_3$, PEG linker. This PEG linker can then be attached to a peptide based fragment to form a Boc-protected aminoxy peptide based compound. Thereafter the Boc-protected aminoxy peptide based compound is synthesized to obtain a radiolabelled peptide based compound that can be used in angiogenesis.

Discussion or citation of a reference herein shall not be construed as an admission that such reference is prior art to the present invention

SUMMARY OF THE INVENTION

The present invention provides a novel intermediate synthesis for obtaining an unsymmetrical PEGylated linker.

One embodiment of the present invention depicts a method for preparing a linker of formula (K1), comprising the following reactions:

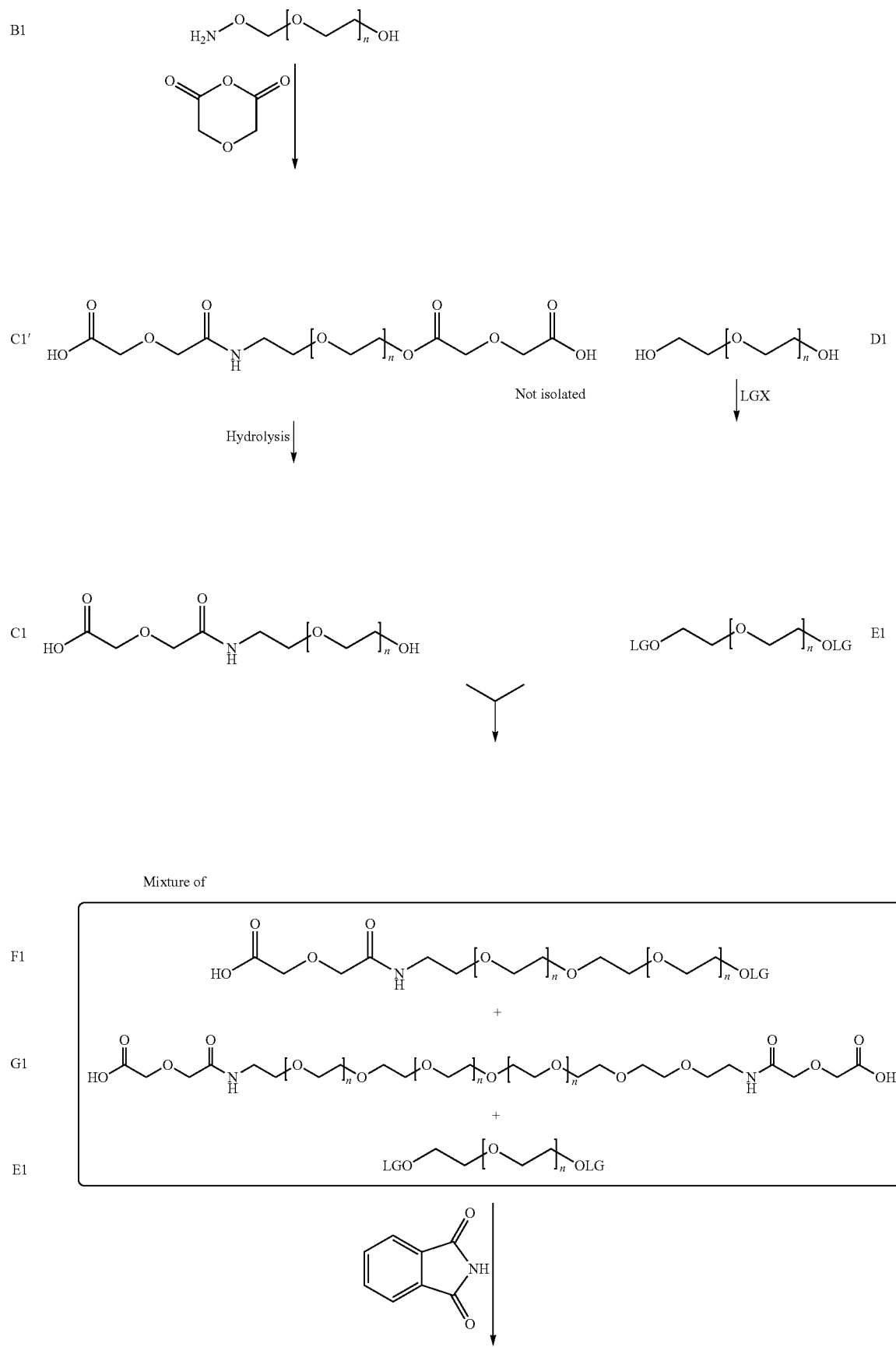

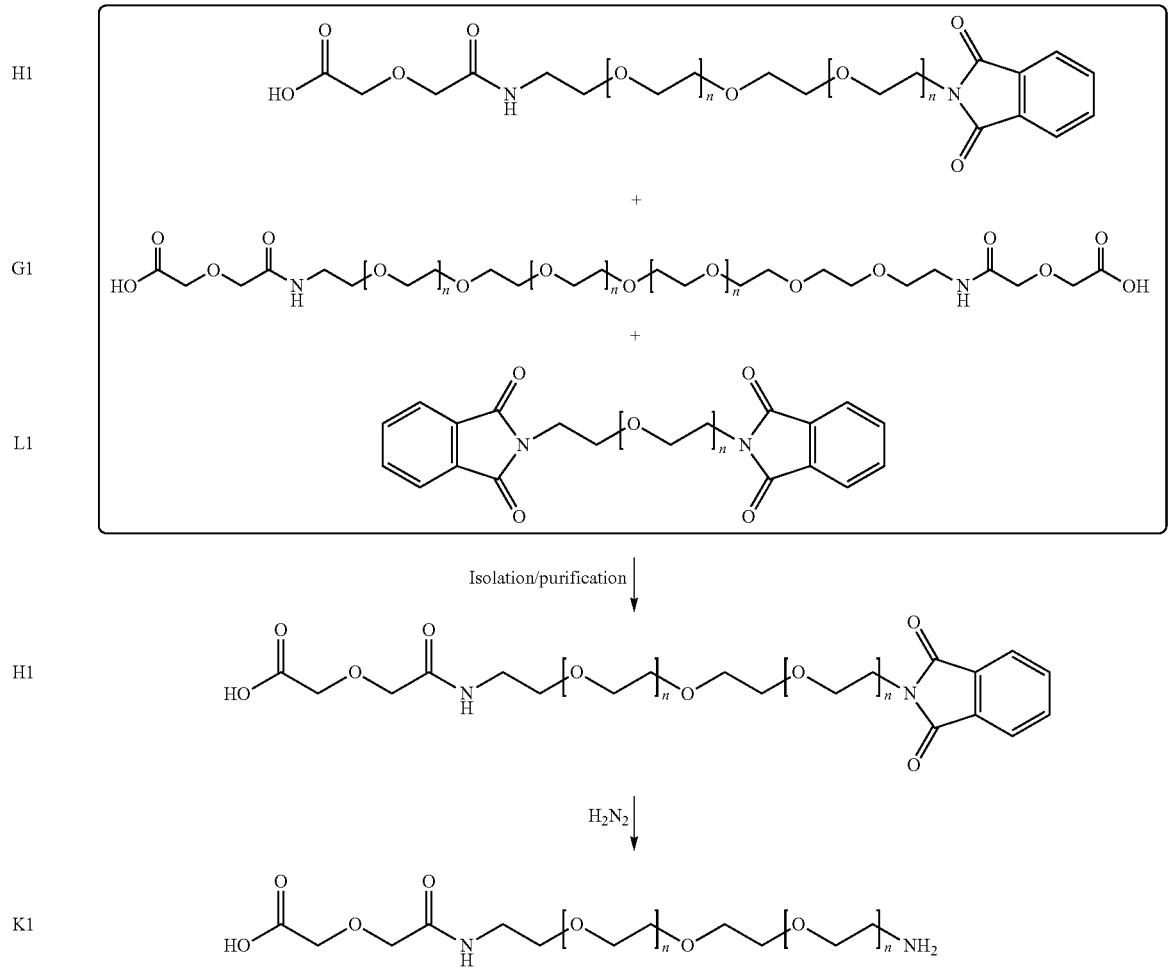

wherein R denotes one of the following structures

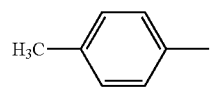 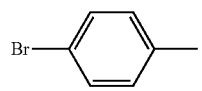

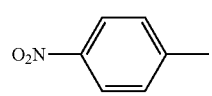  

and
wherein PG can be either a carbamate of the form

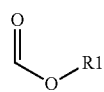

or wherein PG denotes

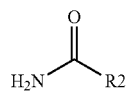

where R2=alkyl or aryl and more preferably R2=H where PG is formyl or R2 is a methyl wherein PG is acetyl and most preferably where R2=phenyl where PG is benzoyl or further wherein PG can be alkyl or aryl and more preferable allyl or most preferable benzyl
and n denotes 1-19.

DETAILED DESCRIPTION OF THE STRUCTURES

Table 1 depicts key selected structures and structure names of the intermediates for making the linker, and starting materials.

DETAILED DESCRIPTION OF THE INVENTION

In preparing angiogenesis radiolabelled products, an important building block in the synthesis of obtaining a radiolabelled peptide based compound is identifying a reliable and efficient linker. In the present invention, even though there is no commercial available reagent for the PEG-linker, a convenient synthesis from commercial cost-effective reagents are disclosed herein. Specifically, the present invention claims novel intermediate synthesis for quickly and efficiently obtaining a PEG linker.

There are advantages for using the claimed synthesis to obtain a PEG linker. One advantage is that the claimed synthesis is a quick process for obtaining a PEG-linker. More specifically, using linker K1, disclosed herein, for large scale production is advantageous from a cost perspective point when using intermediates such as compound F1 and H1.

There are several advantages for synthesizing modified polyethylene glycols to obtain the claimed PEG linker.

One advantage is that the claimed synthesis is a shorter and faster process for obtaining a PEG linker. The convenient synthesis used herein can be carried out in half-a-day thus making it possible to produce a PEG moiety in under one week.

Unless otherwise defined herein below all technical and scientific terms used herein have the same meaning as commonly understood by one of ordinary skill in the art to which the invention pertains.

A PEG (polyethylene glycol) is a chain of individual ethylene glycols.

The term linker as used herein means a moiety that links together at least two other moieties, such as a vector and a reporter. The use of linker groups with different lipophilicities and or charge can significantly change the in vivo pharmacokinetics of a peptide to suit the diagnostic need. A wide variety of linkers may be used, including biodegradable linkers and biopolymers. The linker is at its simplest a bond between the vector and the aminoxy group. More generally, the linker will provide a mono- or multi-molecular skeleton, e.g. a linear, cyclic, or branched skeleton. The linker may further have the role to distance the vector from the reporter. The linker described herein specifically comprises macromolecular structures such as dextran and preferably poly(ethyleneglycols), referred to as PEGs. Linkers including a PEG moiety have been found to slow blood clearance which is desirable in some circumstances. The linker may be derived from glutaric and/or succinic acid and/or a polyethyleneglycol based moiety.

All molecules that have a PEG center moiety of different lengths and a protected aminoxy acetic acid on one side and a spacer connected as an amide to other terminal end of the PEG moiety can be synthesized following the described synthetic protocol accordingly in preparing formula (1) without the use of an azide, the anion with the formula $N_3^-$.

Additionally, the synthetic protocol described below enables formation of PEG moieties of different lengths, i.e. the number of ethylene glycols coupled in series.

A vector is defined herein as a fragment of a compound or moiety having affinity for a receptor molecule, preferably a peptidic species or more preferably an angiogenesis targeting species such as an RGD peptide. A specific example of a vector used herein is an Arg-Gly-Asp peptide or an analogue thereof.

In the synthesis described herein the boxed in part disclosed in the claimed reaction below can be preformed in a one-pot procedure.

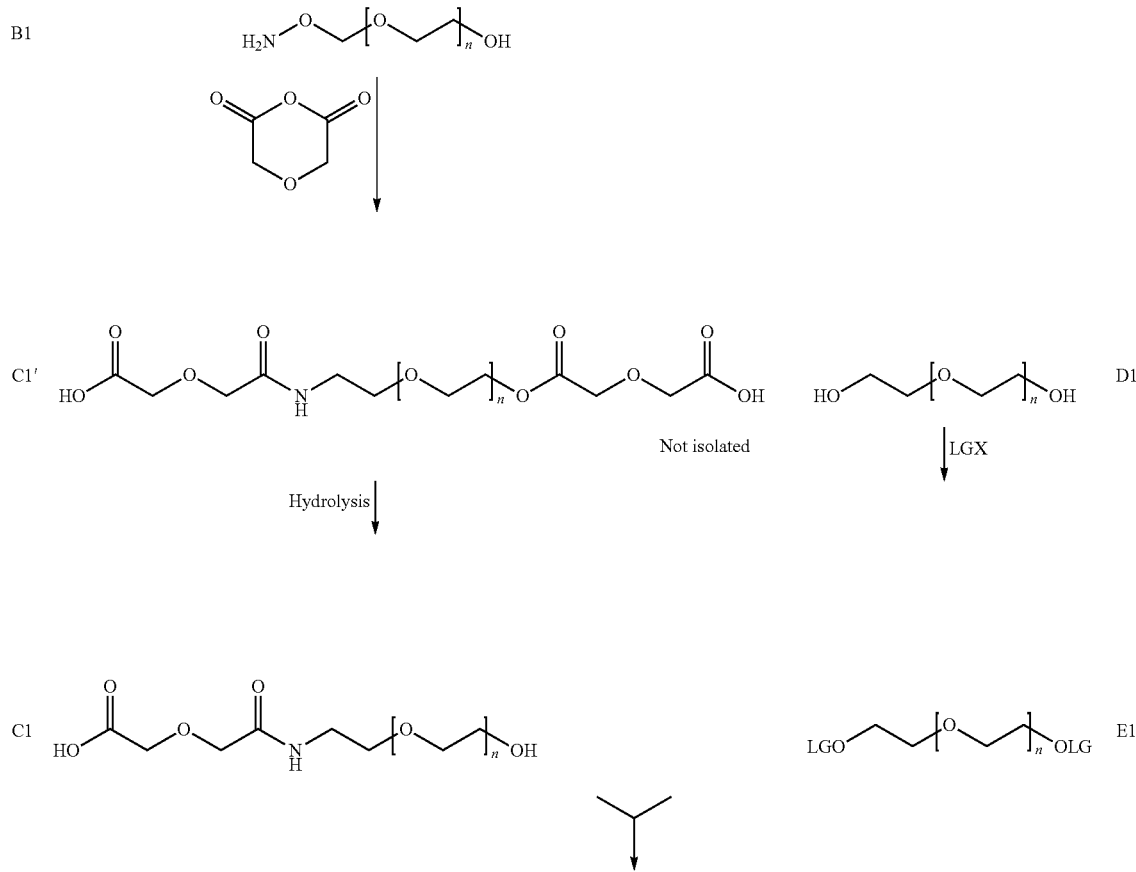

-continued
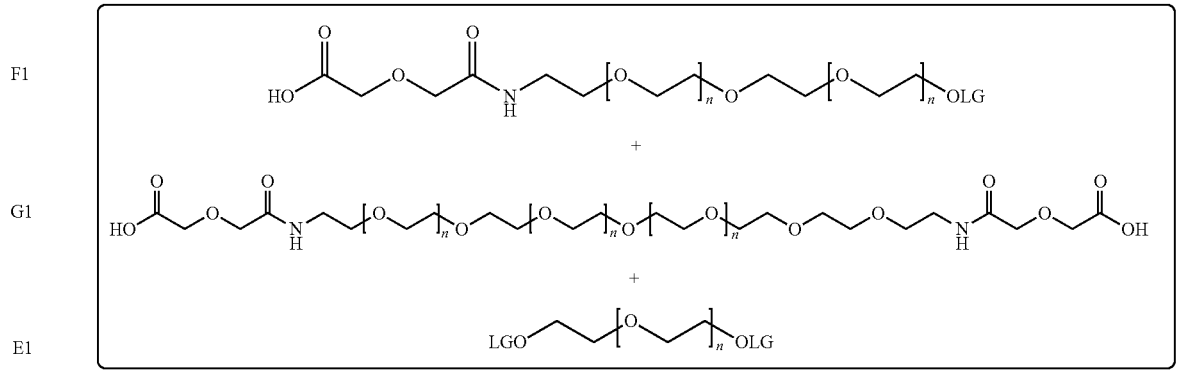
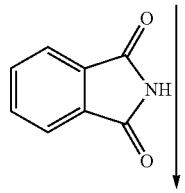
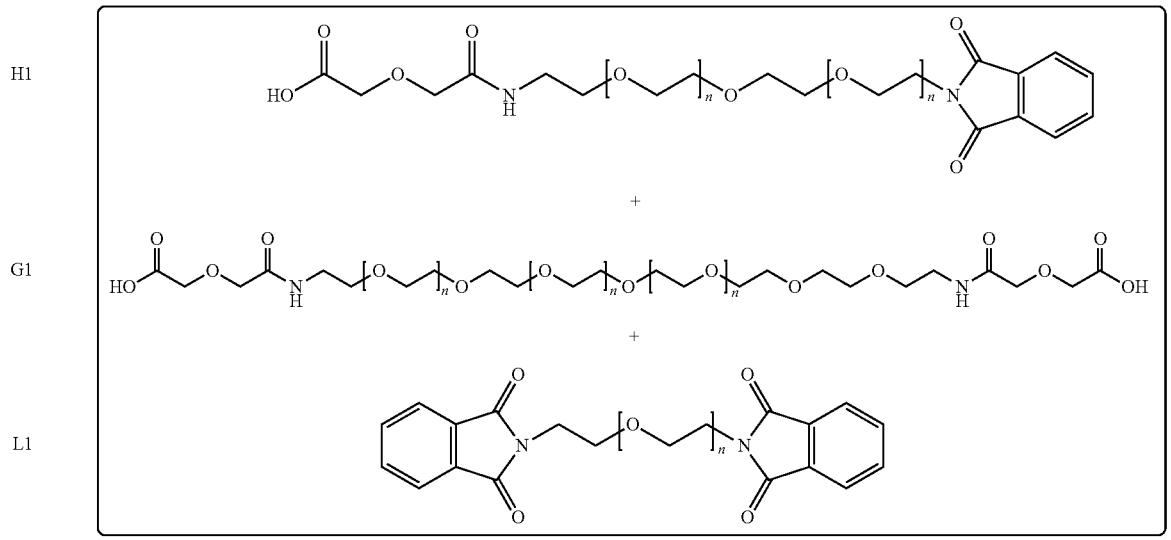
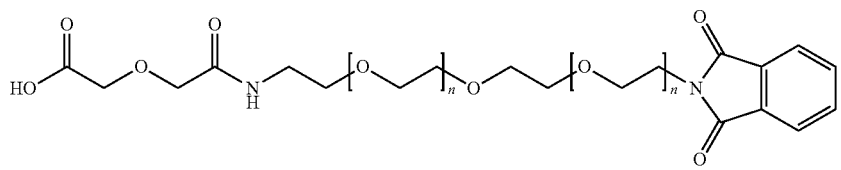
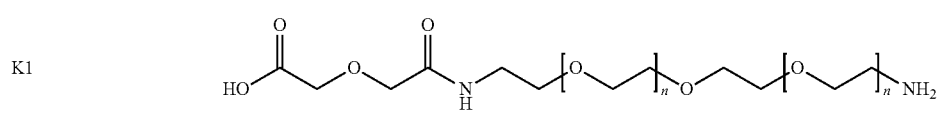

11
wherein R denotes one of the following structures
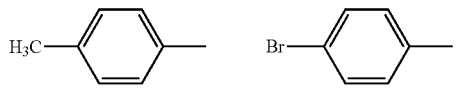
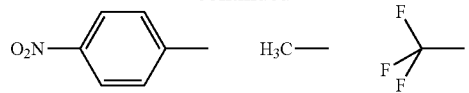
One embodiment of the present invention depicts a method for preparing a linker of formula (K1), comprising the following reactions:
B1 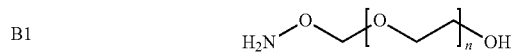
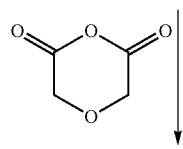
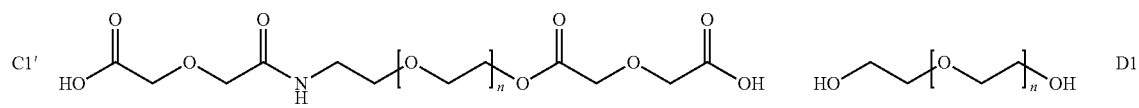
C1' ... Not isolated     D1 ... |LGX
Hydrolysis |
C1 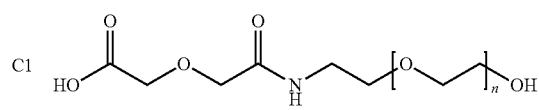     E1 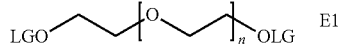
Mixture of
F1 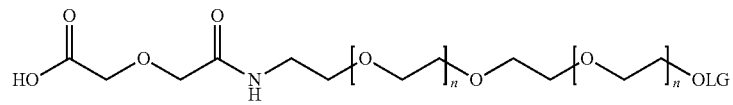
+
G1 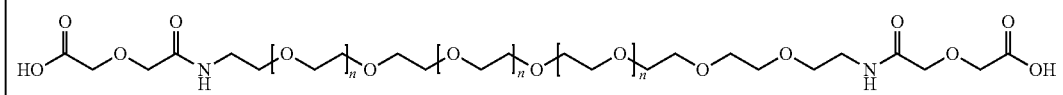
+
E1 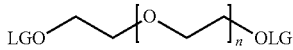
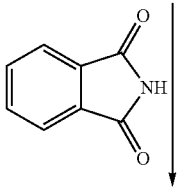

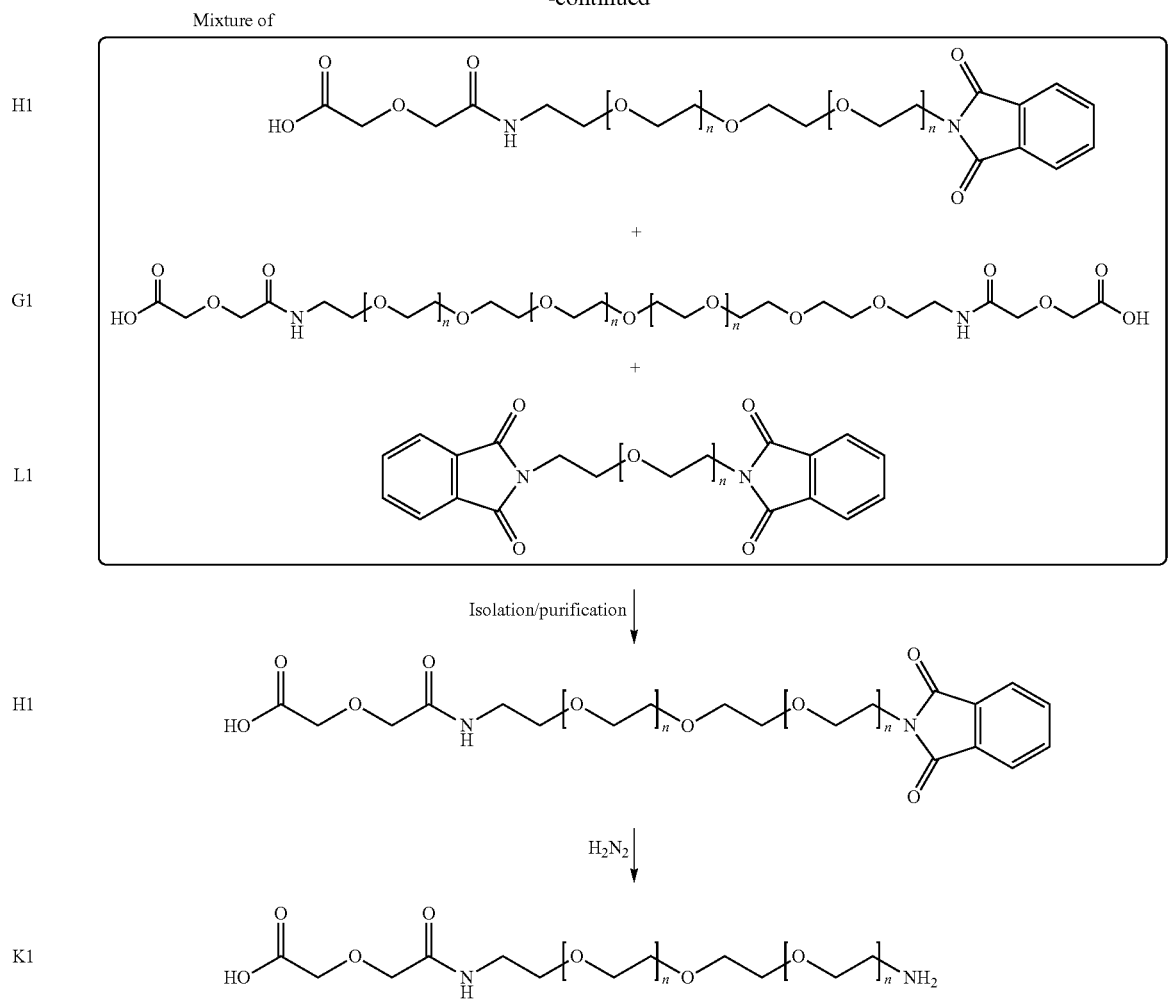

wherein R denotes one of the following structures

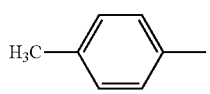 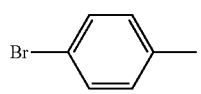

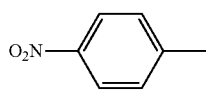  

and
wherein PG can be either a carbamate of the form

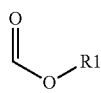

or wherein PG denotes

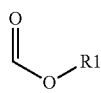

where R2=alkyl or aryl and more preferably R2=H where PG is formyl or R2 is a methyl wherein PG is acetyl and most preferably where R2=phenyl where PG is benzoyl or further wherein PG can be alkyl or aryl and more preferable allyl or most preferable benzyl and n denotes 1-19.

Another embodiment of the present invention depicts a method for preparing compounds E1 and L1 from above wherein the H1 and G1 is separated from L1 by extraction or crystallization.

Yet another embodiment of the present invention depicts a method from the above synthesis wherein C1 reacts with E1 to form a mixture of F1, G1, and E1 wherein E1 is made from a polypropylene glycol by introduction of a leaving group (LG) on both terminal hydroxyl groups.

Still a further embodiment of the present invention shows a method according to the above reaction, wherein the preferred temperature is about 22° C. and the preferred time is about 5-8 hours.

Another embodiment of the present invention shows a method according to the above synthesis, wherein the mixture of F1, G1, and E1 reacts with a phthalimide salt to form a mixture of H1, G1, and L1.

Still another embodiment of the present invention depicts a method according to the above synthesis, wherein the mixture of F1, G1, and E1 reacts with a phthalimide salt to form a mixture of H1, G1, and L1 at a temperature range from about 30° C. to about 70° C. and for about an hour to about four hours.

Yet another embodiment of the present invention shows a method according to the above synthesis, wherein H1 is isolated from G1 by chromatography or crystallization.

EXAMPLES

The invention is further described in the following examples, which are in no way intended to limit the scope of the invention.

The invention is illustrated by way of examples in which the following abbreviations are used:
p: para
o: ortho
HPLC: high performance liquid chromatography
MS: Mass Spectometry
LC-MS: Liquid Chromotography/Mass Spectometry
TEG: tetraethyleneglycol
DMF: Dimethyl formamide
$^{1}$H-NMR: proton nuclear magnetic resonance
THF: Tetrahydrofuran
DMA: Dimethyl acetamide
hr(s): hour(s)
min(s): minute(s)
mg: milligrams
Boc: —COOCH(CH$_3$)$_3$
RT: room temperature
C: temperature in Celsius
M+H$^+$: defined herein as Mass of an ion detected in mass spectrometry as the adduct between a molecule and a proton.
M+Na$^+$: defined herein as Mass of an ion detected in mass spectrometry as the adduct between a molecule and a sodium ion.
UV: ultraviolet
Synthetic Route for the Synthesis of a Boc-Protected Aminoxy Linker A synthetic route for the synthesis of a Boc-protected aminoxy linker is seen in FIG. 1 below. MS and LS-MS were the major analytical tools used for identification of the intermediates.

All synthetic steps were carried out using relatively inexpensive and readily available starting materials and chemicals. None of the steps can be identified as costly or inefficient.

FIG. 1 Synthesis of the Boc-protected aminoxy linker

-continued
Mixture of
F1 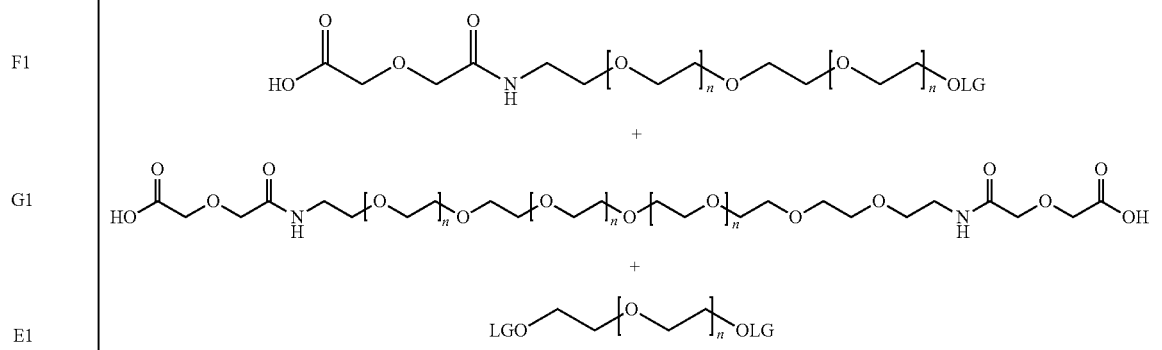
G1
E1
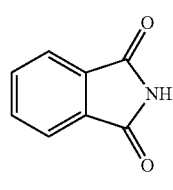
Mixture of
H1 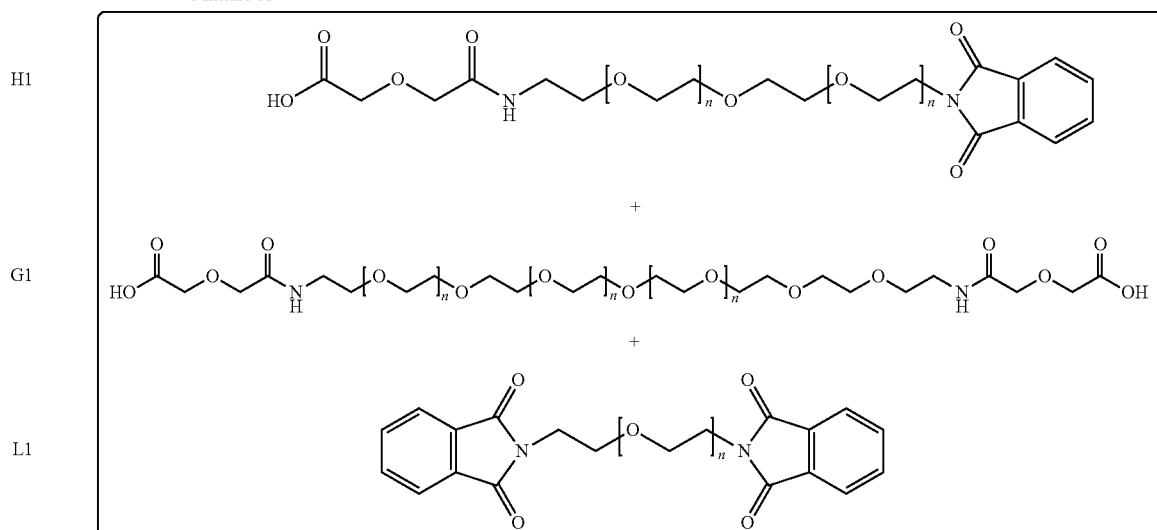
G1
L1
Isolation/purification ↓
H1 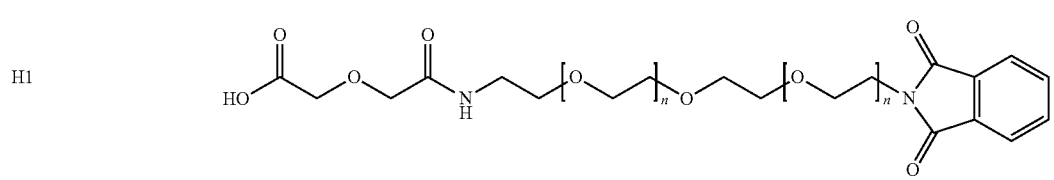
H₂N₂ ↓
K1 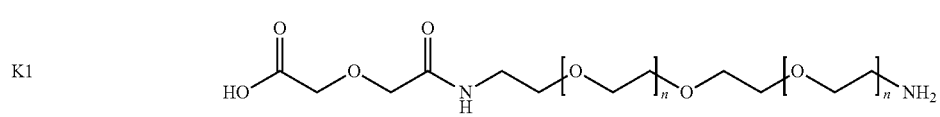

Experimental Data of Each Process Step for the Synthesis of the Boc-Protected Aminoxy Linker N-Acylation with Anhydrides N-acylations with anhydrides are common and convenient synthetic tools for formation of amides from amines.

FIG. 2 N-acylation of 2-(2-amioethoxy)ethanol with glycolic anhydride

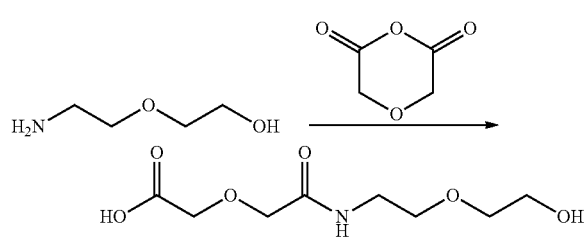

i. 11-O-tosyl-3,6,9-trioxa-1-hydroxy-undecane (3)

1,11-dihydroxy-3,6,9-trioxa-undecane (TEG) (2) chloroform. The reaction mixture was stirred at ambient temperature (20-23° C.) over night. The reaction mixture was thereafter filtered and the filtrate evaporated under reduced pressure. Residue was first mixed and shaken with hexane, thereafter with ethyl acetate/hexane 1:1 and finally the product was extracted from the residue by suspending the residue in ethyl acetate. The suspension was filtered and the product collected in the filtrate. The filtrate was evaporated under reduced pressure and the residue analysed by MS.

The MS Confirmed a Mix of Unreacted, Monotosvlated (M+H$^+$ 349.14) and Ditosvlated (M+H$^+$ 503.15)

ii. Formation N-(3,6,9-trioxa-11-hydroxy-undecane)-phthalimide (4)

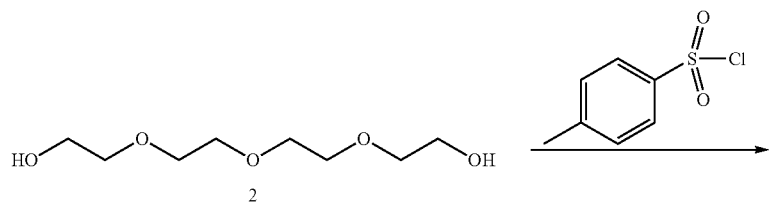

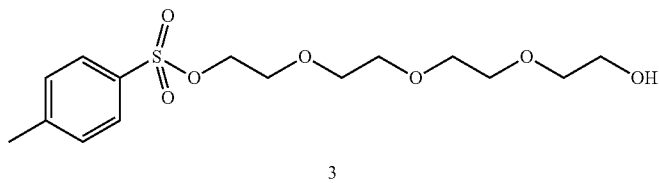

A pre-made solution of p-toluene sulfonylchloride was added dropwise over 60 min to a solution of triethylamine and

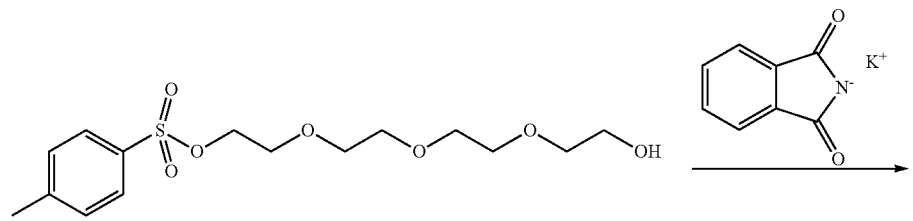

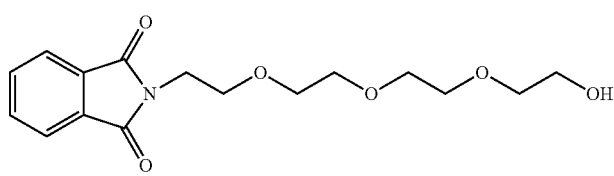

The tosylated TEG (3) from first step was dissolved in DMF and potassium phthalimide and added. The reaction mixture was stirred at 80° C. over night. The morning after the temperature was raised to 90° C. for two hours. After cooling to room temperature the mixture was filtered and the filtrate evaporated under reduced pressure. The residue was mixed with methanol and filtered and the filtrate evaporated under reduced pressure. This procedure was repeated with diethyl ether.

iii. Purification of N-(3,6,9-trioxa-1'-hydroxy-undecane)-phthalimide (4)

The crude N-(3,6,9-trioxa-11-hydroxy-undecane)-phthalimide containing bis-N-phthalimide was dissolved in as little THF as possible. The THF solution was added drop wise to water at 40-60° C. The bisamide precipitated from water and was removed by filtration after cooling. The filtrate was evaporated under reduced pressure and the diethyl ether was added to the residue and product extracted from the solid residue into the diethyl ether. The ether was decanted and the procedure repeated once. The residue was mixed with water and extracted with 1× diethyl ether and 2× ethyl acetate. The combined ethyl acetate phases were evaporated under reduced pressure. The ether phases were combined, decanted and evaporated. The residue was dissolved in ethyl acetate and the solution was added to the product isolated from exhilarate extraction. This second ethyl acetate solution was evaporated under reduced pressure. The structure of 4 was confirmed by $^1$H-NMR.

The ratio between product 4:bisimide:TEG was 86:2:12 (NMR).

iv. 11-amino-3,6,9-trioxa-hydroxy-undecane

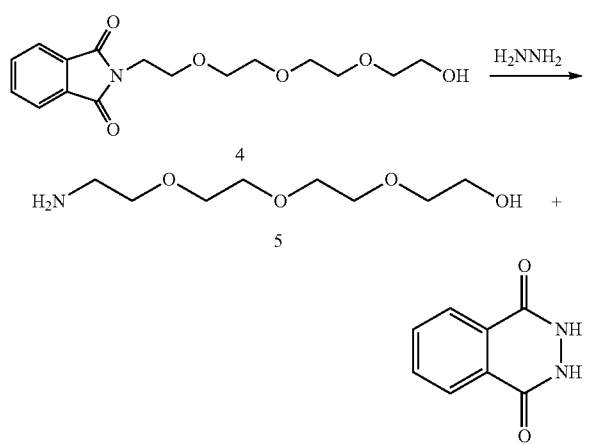

100 mg of compound 4 was dissolved in methanol and hydrazine monohydrate added. The mixture was heated to 50° C. for 3 hours, cooled to room temperature and stirred at room temperature over night.

MS confirmed desired product (M+H$^+$ 194.1).

v. 17-hydroxy-3,9,12,15-tetraoxa-6-aza-5-oxo-heptadecanoic acid (6)

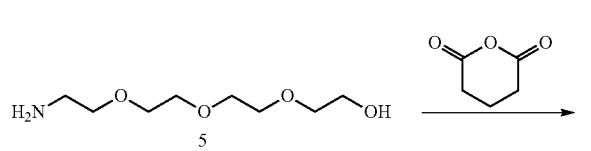

-continued

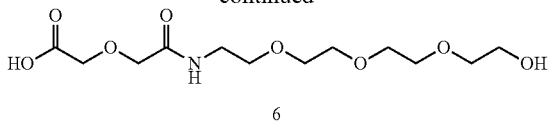

The amine 5 was mixed with dichloromethane and some DMF as co-solvent. 1.5 mole eqv. diglycolic anhydride wad added and the mixture heated to 40° C. for a couple of hours. After cooling to room temperature and stirring over weekend the reaction mixture was evaporated under reduced pressure. The residue was mixed with water and pH adjusted to pH between 11-12 with 1N NaOH$_{(aq)}$ for hydrolysis of the ester. The solution was allowed to stir over night and was thereafter acidified with HCl to pH 1-2 and evaporated under reduced pressure.

LC-MS of the residue showed a major peak with the expected masses M+H$^+$ 310.15 and M+Na$^+$ 332.13.

vi. (Boc-aminooxy)acetic anhydride (8)

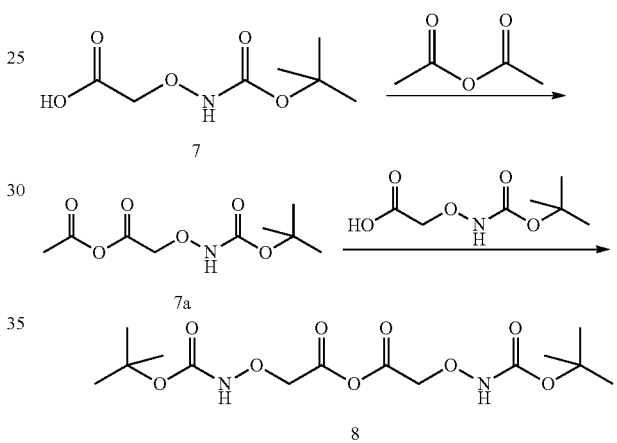

(Boc-aminooxy)acetic acid (7) was dissolved in acetic anhydride and heated to 50-60° C. over the weekend. LC-MS of the reaction mixture showed several different products including the mixed anhydride 7a and the symmetric anhydride 8.

The anhydride 7a was originally the target compound, however, 8 was found in the reaction mixture and is a better reagent than 7a for the next step (see above) since N-acylation with 7a can give two different products; N-(boc-aminooxy)acetamide as the wanted product and N-acetamide as by-product.

Structure of compound 8 was confirmed by LC-MS (M+H$^+$ 365) fragments with M+H$^+$ 265.1 and M+H$^+$ 165 indicated the loss of one and two Boc-groups.

vii. 5-N-(Boc-aminooxy-acetamide)-3-oxa-1-hydroxypentan (9)

-continued

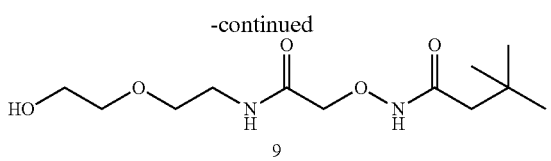
9

A mixture containing compound 8 was dissolved in THF and 2(2-aminoethyl)ethanol added. The reaction mixture was stirred at room temperature for 3 days. The reaction mixture was mixed with water and pH adjusted to above 10 with NaOH$_{(aq)}$ and stirred over night. The reaction mixture was added to THF and brine and extracted. The evaporated THF phase was used directly in the next step.

Product was identified using LC-MS.

viii. 5-N-(Boc-aminooxy-acetamide)-3-oxa-1-(O-tosyl)pentane(9)

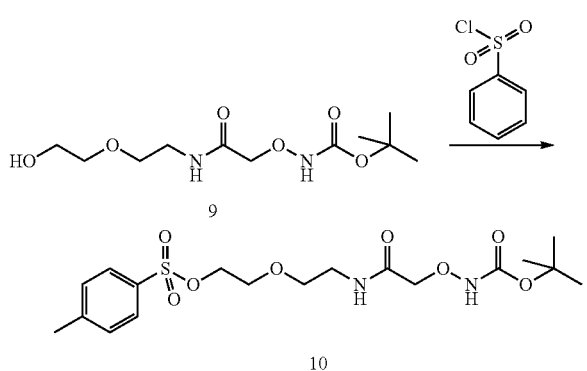

Discussion/Results

The target compound a Boc-protected aminoxy linker is to be made by coupling between intermediate 6 and 10. Results for the experiments shows that both compound 6 (4 synthetic steps) and 10 (3 synthetic steps) can be made by simple synthetic methods. Compound 10 was made in three synthetic steps without any form for purification. The ether formation using the suggested method was confirmed in experiment ix above.

An important step in the synthesis is formation of compound 9. There are several approaches to perform this. One is to make the acid halide of compound 7, however, the Boc group is not to stable during e.g. acid chlorination. One other method is to use coupling reagents. A problem using couplings reagents is the low molecular weights of product and reagents.

The formation of compound 8 might be the better solution and the formation is proved in experiment vi, see above. Tuning of this synthesis to give a relatively pure compound 8 seems to be the key for success. A follow-up on this step is done by using an in-situ made mixed anhydride between formic- and acetic acid. The higher reactivity of formyl over acetyl would give a mixed anhydride between 7 and formyl. The formyl group is less stable than acetyl and the formation of 8 should be favored if 7 is present. The anhydride 8 is regarded as the thermodynamic preferred structure over the mixed anhydrides.

Specific Embodiments, Citation of References

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

TABLE 1

Selected structures and structure names of products, starting materials and intermediates

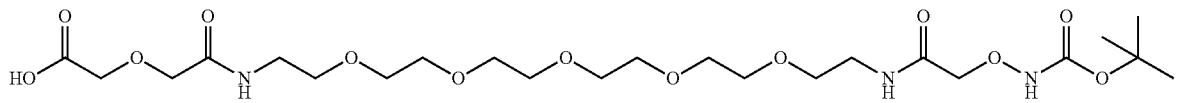

23-(Boc-aminooxyacetyl-amino)-5-oxo-6-aza-3,9,12,15,18,21-hexaoxatriconsanioc acid

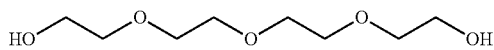

1,11-dihydroxy-3,6,8-trioxa-undecane

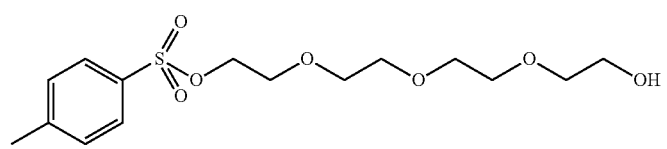

11-O-tosyl-3,6,9-trioxa-1-hydroxy-undecane

TABLE 1-continued
Selected structures and structure names of products, starting materials and intermediates
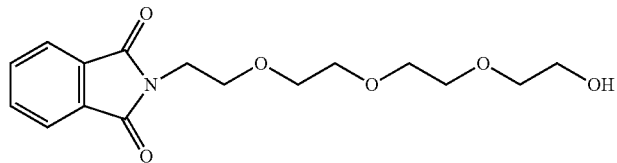
N-(3,6,9-trioxa-11-hydroxy-undecane)-phthalimide
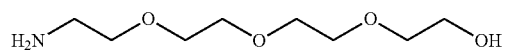
11-amino-3,6,9-trioxa-hydroxy-undecane
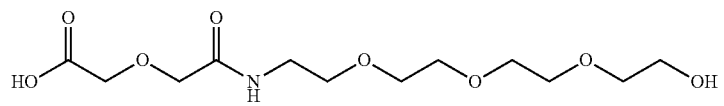
17-hydroxy-3,9,12,15-tetraoxa-6-aza-5-oxo-heptadecanoic acid
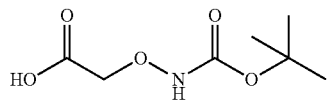
(Boc-aminooxy)acetic acid
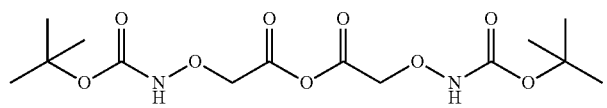
(Boc-aminooxy)acetic anhydride
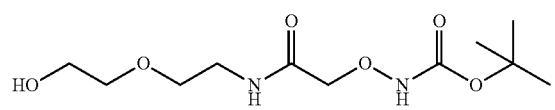
5-N-(Boc-aminooxy-acetamide)-3-oxa-1-hydroxypentane TABLE 1-continued Selected structures and structure names of products, starting materials and intermediates

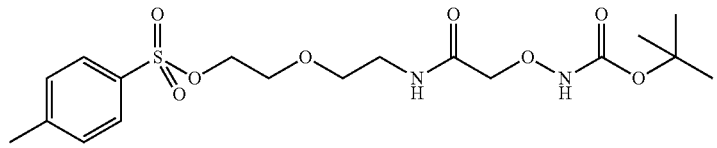

N-(Boc-aminooxy-acetamide)-3-oxa-1-(O-tosyl)pentane

Reagents: (only those directly involved in reaction, bases, solvent, etc. included)

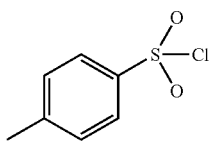

p-toluene sulfonylchloride

H₂NNH₂
Hydrazine

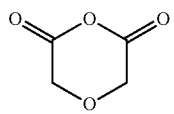

diglycolic anhydride

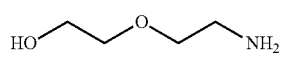

2(2-aminoethyl)ethanol

Base to be used in final step: LDA
Lithium diisopropylamine

What is claimed is:
1. A method for preparing an unsymmetrical linker compound of formula (K1), which comprises the following reactions:
B1 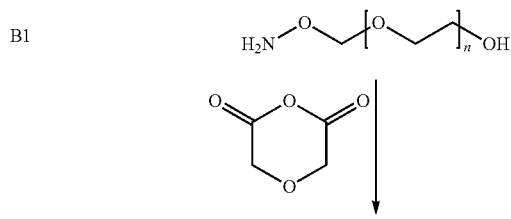
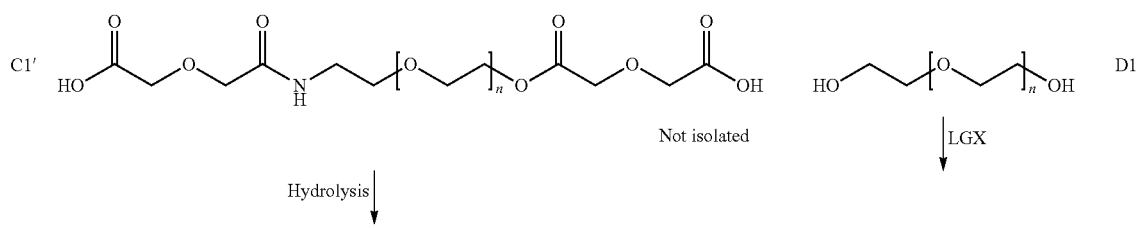
Not isolated
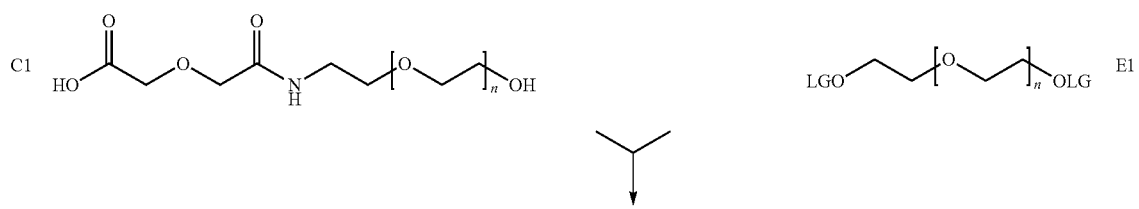
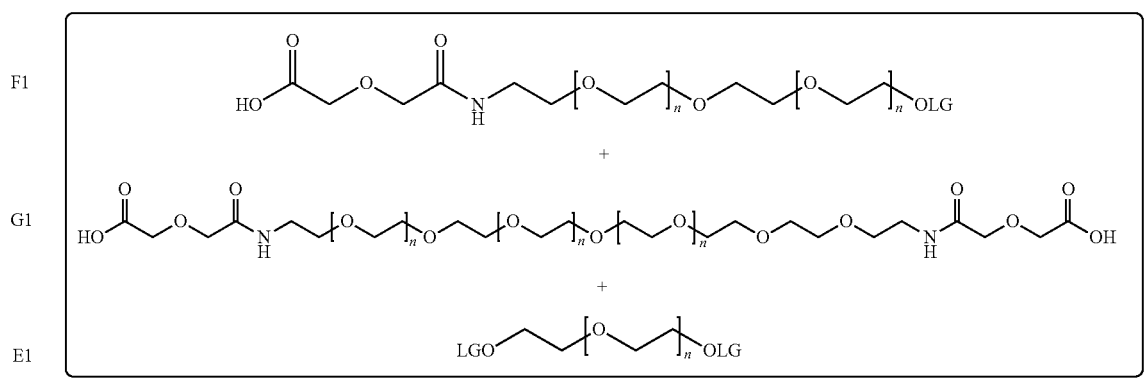
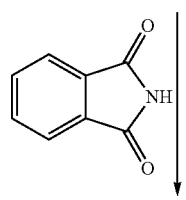

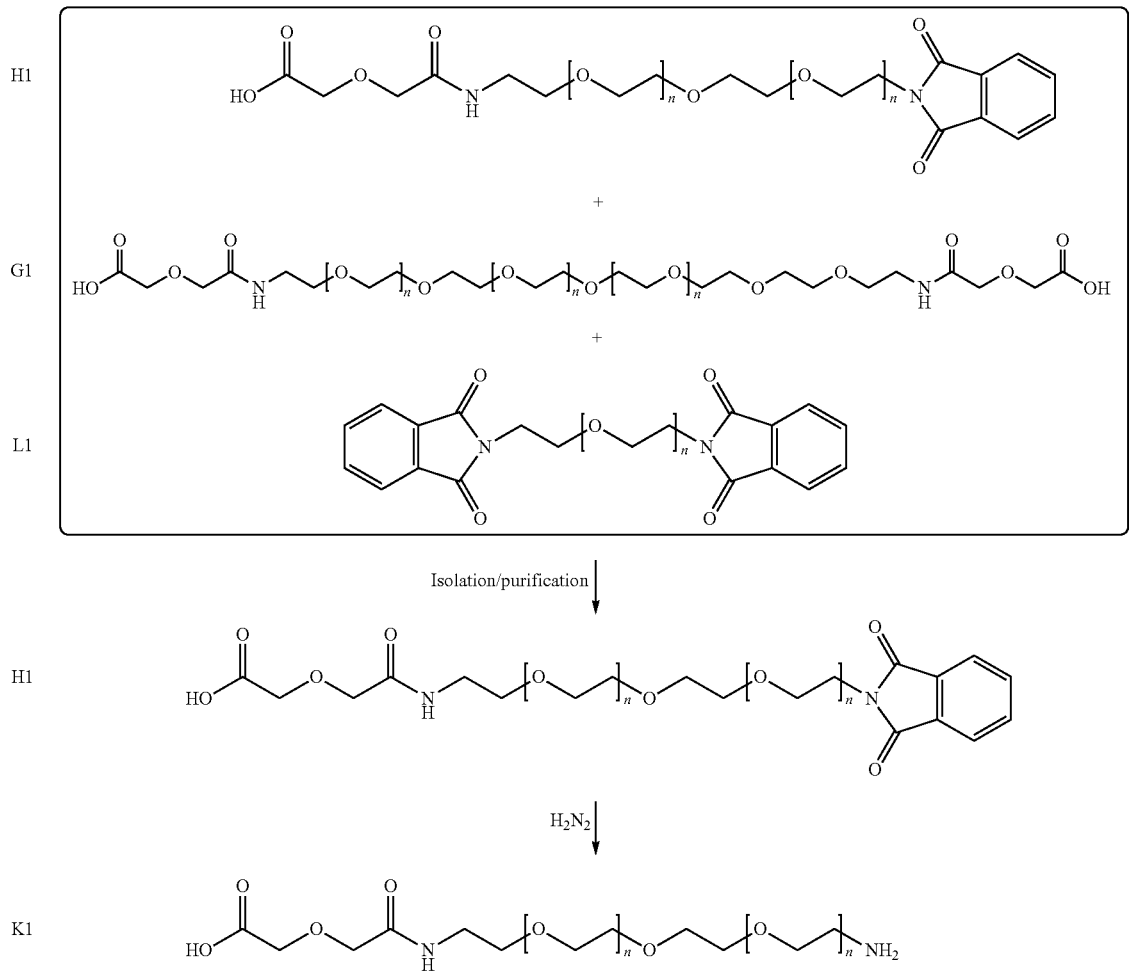

wherein:
LG is a leaving group; and
n denotes 1-19.

2. The method for preparing compounds E1 and L1 of claim 1, wherein H1 is separated from G1 and L1 by extraction or crystallization.

3. The method of claim 1, wherein E1 is made from a polypropylene glycol by introduction of a leaving group (LG) on both terminal hydroxyl groups.

4. The method of claim 1, wherein C1 reacts with E1 to form a mixture of F1, G1 and E1.

5. The method of claim 1, wherein the mixture of F1, G1, and E1 reacts with a phthalimide salt to form a mixture of H1, G1, and L1.

6. The method of claim 5, wherein the mixture of F1, G1, and E1 reacts with a phthalimide salt to form a mixture of H1, G1, and L1 at a temperature range from about 30° C. to about 70° C. and for about an hour to about four hours.

7. The method of claim 4, wherein the preferred temperature is about 22° C. and the preferred time is about 5-8 hours.

* * * * *